United States Patent [19]

Barnaby

[11] Patent Number: 4,539,837

[45] Date of Patent: Sep. 10, 1985

[54] DRIVEN-CAPILLARY VISCOSIMETER

[75] Inventor: Harold T. Barnaby, Duncanville, Tex.

[73] Assignee: Core Laboratories, Inc., Dallas, Tex.

[21] Appl. No.: 641,688

[22] Filed: Aug. 17, 1984

[51] Int. Cl.³ .............................................. G01N 11/04
[52] U.S. Cl. ............................................. 73/55; 73/54
[58] Field of Search ................................. 73/55, 54, 56

[56] References Cited

U.S. PATENT DOCUMENTS

| | | | |
|---|---|---|---|
| 2,431,378 | 11/1947 | Eitzen et al. | 73/57 |
| 2,934,944 | 5/1960 | Eolkin | 73/55 |
| 2,948,145 | 9/1960 | Eolkin | 73/54 |
| 3,086,386 | 4/1963 | Kapff | 73/54 |
| 3,111,838 | 11/1963 | Bucalo | 73/54 |
| 3,286,511 | 11/1966 | Harkness | 73/55 |
| 3,327,522 | 6/1967 | Hoyt | 73/55 |
| 3,468,158 | 9/1969 | Sze-Foo Chien | 73/55 |
| 3,559,464 | 2/1971 | Foust et al. | 73/55 |
| 3,745,811 | 7/1973 | Dure et al. | 73/54 |
| 3,990,295 | 11/1976 | Renovanz et al. | 73/55 |
| 4,313,339 | 2/1982 | Nichols et al. | 73/56 |

FOREIGN PATENT DOCUMENTS

| | | | |
|---|---|---|---|
| 2452442 | 5/1976 | Fed. Rep. of Germany | 73/55 |
| 763744 | 9/1980 | U.S.S.R. | 73/55 |

*Primary Examiner*—Stewart J. Levy
*Assistant Examiner*—Hezron Williams
*Attorney, Agent, or Firm*—Lee C. Robinson, Jr.

[57] ABSTRACT

A viscosimeter measures the viscosity of a fluid, such as a petroleum hydrocarbon liquid, by driving a capillary through the fluid and measuring the pressure drop across the capillary. The viscosimeter comprises a pressure cylinder, a piston within the cylinder having at least one capillary tube, and an arrangement for driving the piston at a known speed so that the fluid is displaced at a known volumetric rate through the capillary tube. Pressure sensors on either end of the cylinder measure the capillary pressure drop. In a preferred embodiment, the piston has a main body and a selector plate. The main body has a plurality of capillary tubes each of a different bore size, and the selector plate is rotatable relative to the main body by rotating a selector handle outside the cylinder. An oven enclosure permits the cylinder, and its fill of fluid, to be heated in an air bath to reservoir temperatures.

14 Claims, 8 Drawing Figures

DRIVEN-CAPILLARY VISCOSIMETER

This invention relates to viscometry, that is, to the measurement of viscosity of a fluid such as petroleum. The invention is more particularly directed to the measurement of viscosity using a capillary-tube viscosimeter.

In the exploration for oil, as well as in the evaluation of existing oil fields to determine the cost-effectiveness of the pumping of petroleum, it is necessary to measure accurately the viscosity of the liquid hydrocarbons found beneath the earth's surface. These liquid hydrocarbons may have viscosities ranging as high as 10,000 centipoise. In order to be relevant to field conditions, the viscosity should be measured at the temperature and pressure that are characteristic of the subsurface conditions to which the liquid petroleum materials are subjected in nature.

Many viscosimeters (sometimes called viscometers) have been previously proposed for accurate measurement of the viscosity of a fluid. Of these, several previously-proposed viscosimeters force the fluid through a capillary tube arrangement and produce a pressure signal corresponding pressure drop across the capillary tube. From this, the fluid viscosity can be derived. In other arrangements, a constant pressure head is maintained to force the fluid materials through a capillary, and the rate of flow and the pressure are measured.

In the above-mentioned capillary-tube viscosimeters, the values corresponding to the pressure head, the radius of the capillary tube, the length of the capillary tube, and the rate of flow of the fluid through the capillary tube are employed in the calculation of viscosity of the fluid according to the well-known Poiseuille's equation, described in the text to follow. Because Poiseuille's equation postulates laminar flow of the fluid through the capillary tube, it is essential to create laminar flow conditions. This means that the rate of flow of fluid through the capillary tube should be even throughout the measurement, and that the pressure head should be maintained constant.

Capillary tube viscometry, and problems associated with it, are discussed in Giddings et al., Development of High-Pressure Capillary-Tube Viscometer and its Application to Methane, Propane, and their Mixtures in the Gaseous and Liquid Regions, 45 J.Chem.Phys. (578-586) July 15, 1966.

In many previously-proposed capillary-tube viscosimeters, changes in the surface tension of the fluid affect the resulting measurements adversely. This is especially true when the measurements are made under high-pressure conditions, as the apparatus is often not sufficiently sensitive to detect small changes in the pressure signal.

A mercury-type viscosimeter was described in U.S. Pat. No. 4,426,878, that viscosimeter being formed of a first cell containing mercury, or another electrically conductive fluid, and a second cell containing a sample of the fluid whose viscosity was to be measured. A passage was provided between the top and the bottom of each of the cells, with a capillary tube disposed near or within the passage at the top of the cells. The mercury or other driving fluid forced the other fluid from one cell to the other through the capillary passage. The height of the mercury column in the first cell determined the pressure head across the capillary tube, and the rate at which the mercury rose to contact in the second cell corresponded to the rate of fluid flow through the capillary passage.

The arrangement of U.S. Pat. No. 4,426,878 is satisfactory for an initial measurement and several subsequent tests. However, it is difficult to keep the mercury-oil interface clean, and when the interface is contaminated, the contacts can become dirty and cannot reliably detect the rise of the mercury column. Additionally, the viscosimeter of U.S. Pat. No. 4,426,878 is rather difficult to load. Also, if it is desired to use a constant-shear-rate device, rather than the arrangement of U.S. Pat. No. 4,426,878, it is necessary to add additional elements, thus making the apparatus rather complex.

Accordingly, it is an object of this invention to provide a new and improved viscosimeter for determining the viscosity of a fluid.

More specifically, it is an object of this invention to provide such a viscosimeter which is suitable for the measurement of viscosity of petroleum liquids, especially under temperature and pressure conditions simulating natural conditions under the earth's surface.

It is another object of this invention to provide a viscosimeter in which the flow of the fluid through the capillary tube is controlled to be substantially constant, and which facilitates reliable measurement of the pressure head across the capillary tube.

It is yet another object of this invention to provide a capillary-tube viscosimeter in which loading and unloading of the fluid to be tested is facilitated.

It is still another object of this invention to provide a viscosimeter in which any of various capillary tubes having different parameters can be selectively employed, in which the selection of the capillary tube is carried out externally of the viscosimeter, and in which the selection can be made even while the viscosimeter contents are under pressure.

It is another object of this invention to provide a viscosimeter in which any of various capillary tubes having different parameters can be selectively employed without disturbance to temperature, pressure, volume, phase condition or equilibrium state of petroleum liquids.

In one illustrative embodiment of this invention, a differential-pressure capillary-tube viscosimeter comprises a hollow pressure cylinder, and a piston disposed for axial movement in the cylinder and sealably contacting the interior wall thereof. The piston has at least one capillary passage extending axially through the piston to permit flow through of the fluid to be tested. In this viscosimeter, it is the capillary that is driven through the fluid, as opposed to the conventional technique of having the fluid forced through the capillary. In order to effect this, a driving arrangement is provided for driving the piston at a controlled speed axially within the cylinder. As the piston moves, the fluid is displaced from one end to the other end of the cylinder through the capillary passage. Pressure detectors or pressure sensors are disposed at or near the ends of the cylinder and in communication with the fluid. Together, these detectors measure the fluid pressure differential across the capillary passage while the piston is being driven.

The driving arrangement moves the piston at an accurately calibrated predetermined rate. As the diameter of the cylinder interior is known, the rate of movement of the piston is proportional to the volumetric rate of flow Q of the fluid through the capillary passage. The effective radius R of the capillary passage and its length L are also known. The differential pressure ΔP will be the difference in pressure between the two ends of the cylinder, as measured by the pressure detectors. These data are then supplied to a suitably-programmed computing device, which can automatically provide the viscosity $\mu$ of the fluid in terms of Poiseuille's equation $$\mu = \frac{\pi \Delta P R^4}{8 L Q}$$

In standard notation, the viscosity $\mu$ is expressed in Poises, or dyne-seconds per square centimeter. The pressure head ΔP is expressed in dynes per square centimeter, the radius of the capillary passage R in centimeters, the length thereof L in centimeters, and the rate of flow Q of fluid in cubic centimeters per second.

From inspection of the above equation, it should be apparent that the viscosity $\mu$ varies with the fourth power of the capillary radius R. Accordingly, for accurate measurement of viscosity over a wide range of fluid viscosities, it is convenient to have available capillary tubes of various radii R, and to select one or more radii suitable for the fluid being tested. Employment of more than one capillary for a viscosity test gives a convenient means for verifying capillary performance and system integrity. Under test conditions where the flow rate Q is held constant, a change in capillary radius will yield a change in differential pressure and flow frictional factor for a specific viscosity. This invention permits the same multiple capillary tube viscosity test under conditions of constant differential pressures, where the result is a change in flow rate Q. These features permit the fluid viscosity examination to be conducted at any Reynolds number value in the laminar flow range, with extension into the turbulent zone, applying different appropriate mathematical computations.

In order to achieve this advantage with a preferred embodiment, the piston includes a main piston body having a plurality of capillary passages disposed circumferentially about the axis of the piston, with each extending axially through the main piston body. The piston further includes a selector plate having an aperture therethrough, the aperture being alignable with a selected one of the capillary passages of the main piston body. The alignment of the selector plate aperture with the main selected capillary passage permits the fluid to flow through, and only through, the selected capillary passage.

To cooperate with these elements, a selecting shaft extends axially out an end of the cylinder, and this shaft is coupled to a selector device, so that the shaft and the main piston body can be selectively rotated relative to the selector plate. Favorably, this selector device includes a selector handle mounted on the selector shaft outside the cylinder.

In order to simulate the underground conditions in which the fluid finds itself in nature, the viscosimeter cylinder is adapted to withstand high pressures, and the viscosimeter assembly also includes an oven enclosure surrounding the cylinder. A bath of hot air in the oven enclosure maintains the cylinder, and the fluid within it, at approximately reservoir temperature. The selector arrangement can be rotated, even under temperature and pressure conditions, so that the capillary tube can be changed at any time during a test.

The foregoing and many other objects, features, and advantages of this invention will be more completely understood from the ensuing detailed description of a preferred embodiment, the description to be considered in connection with the accompanying drawings, in which.

Figure 1:
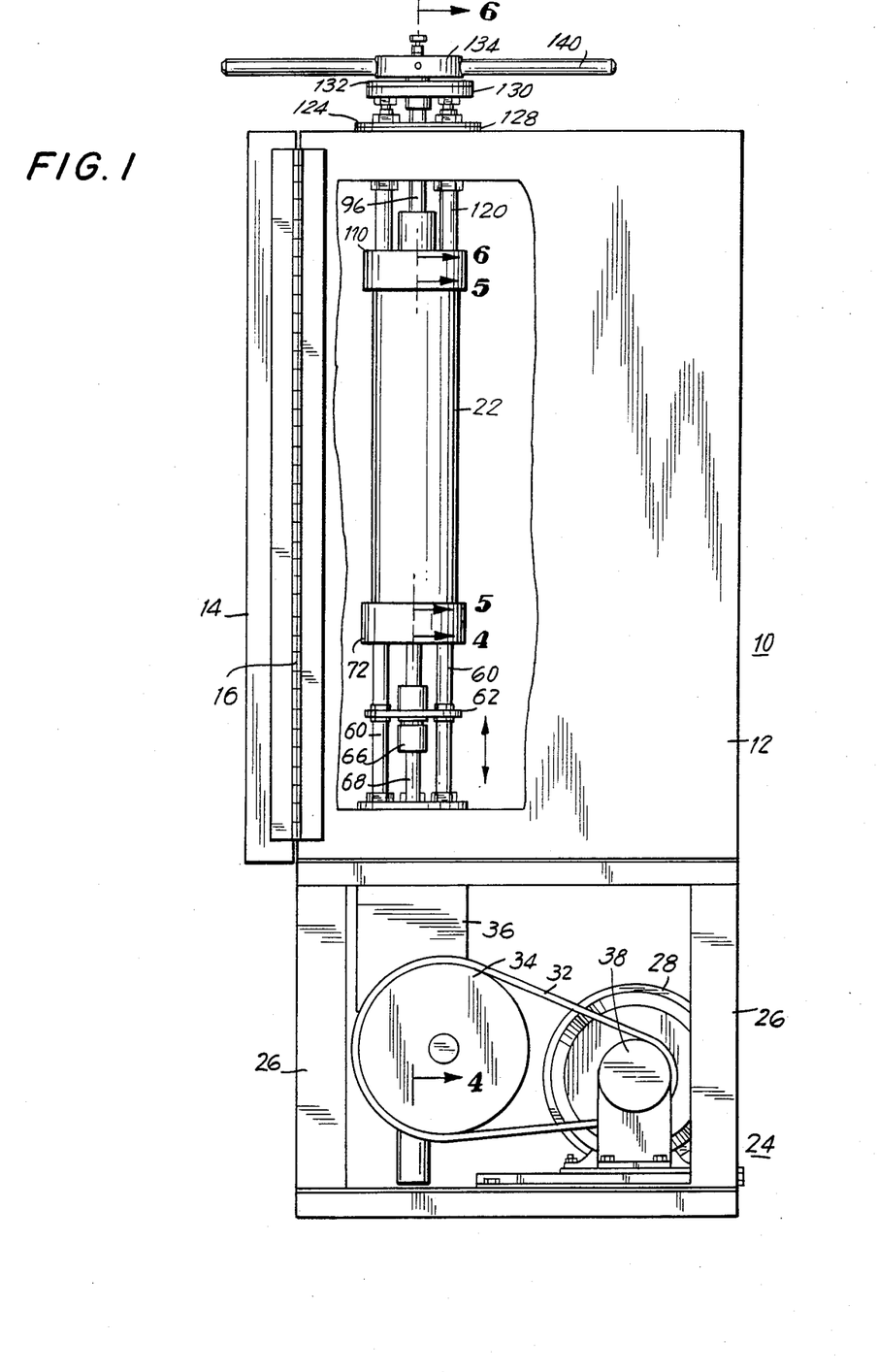
FIG. 1 is a side elevational view, partially cut away, of a capillary-tube viscosimeter according to an embodiment of this invention.
Figure 2:
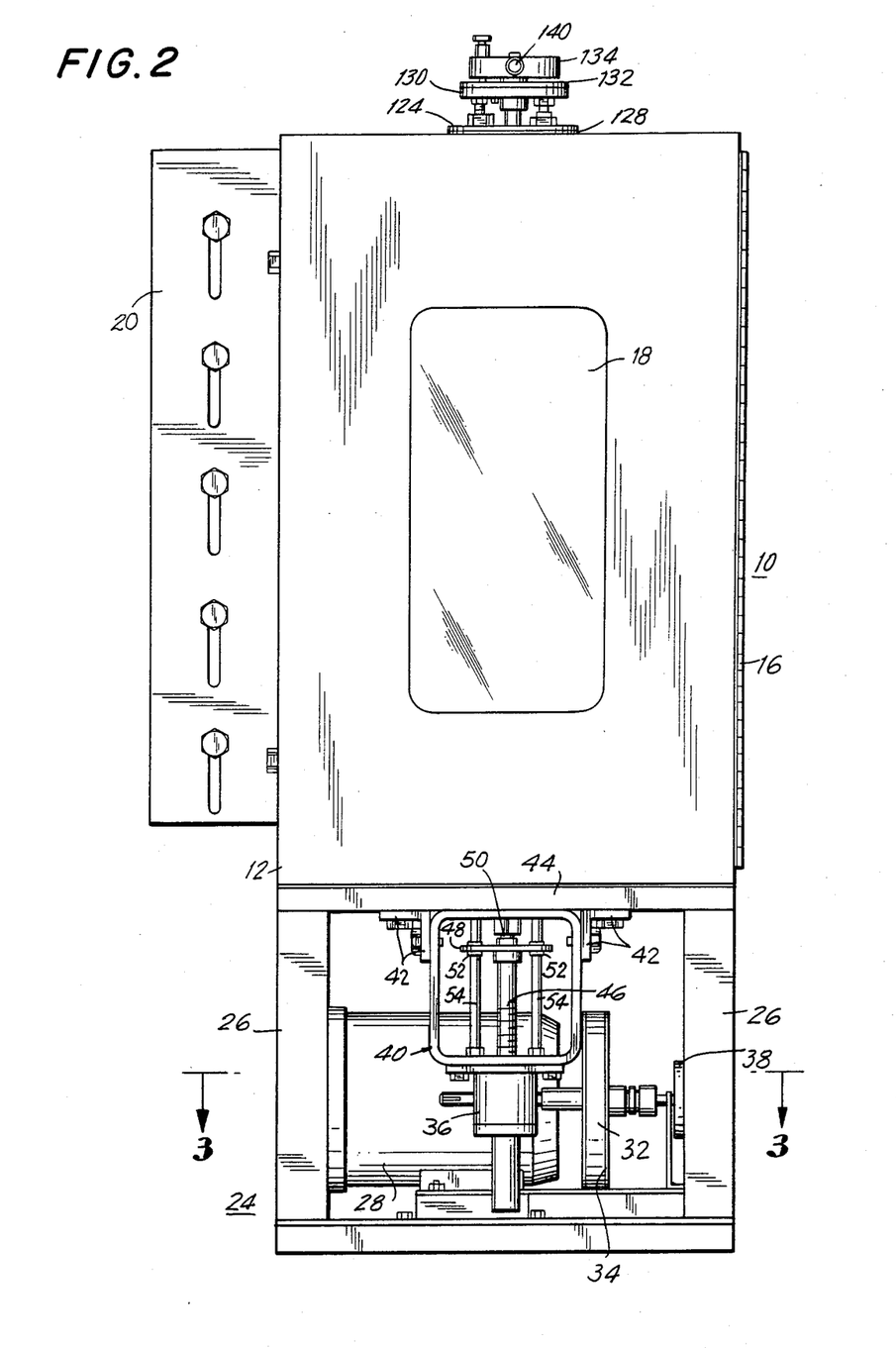
FIG. 2 is a front elevational view of the preferred embodiment of this invention.

With reference to the drawings, and initially to FIGS. 1 and 2 thereof, a viscosimeter assembly 10 includes an oven enclosure 12 having a front oven door 14 coupled to it by means of a piano hinge 16. A glass window 18 on the door 14 permits viewing of the apparatus within the oven enclosure 12, and a wall mount 20 facilitates the mounting of this oven enclosure 12 on a suitable support structure. Within the oven enclosure 12 is a viscosimeter cylinder 22.

A base assembly 24 supporting the oven enclosure 12 includes four stanchions 26, each disposed at a corner of the oven enclosure 12.

Figure 3:
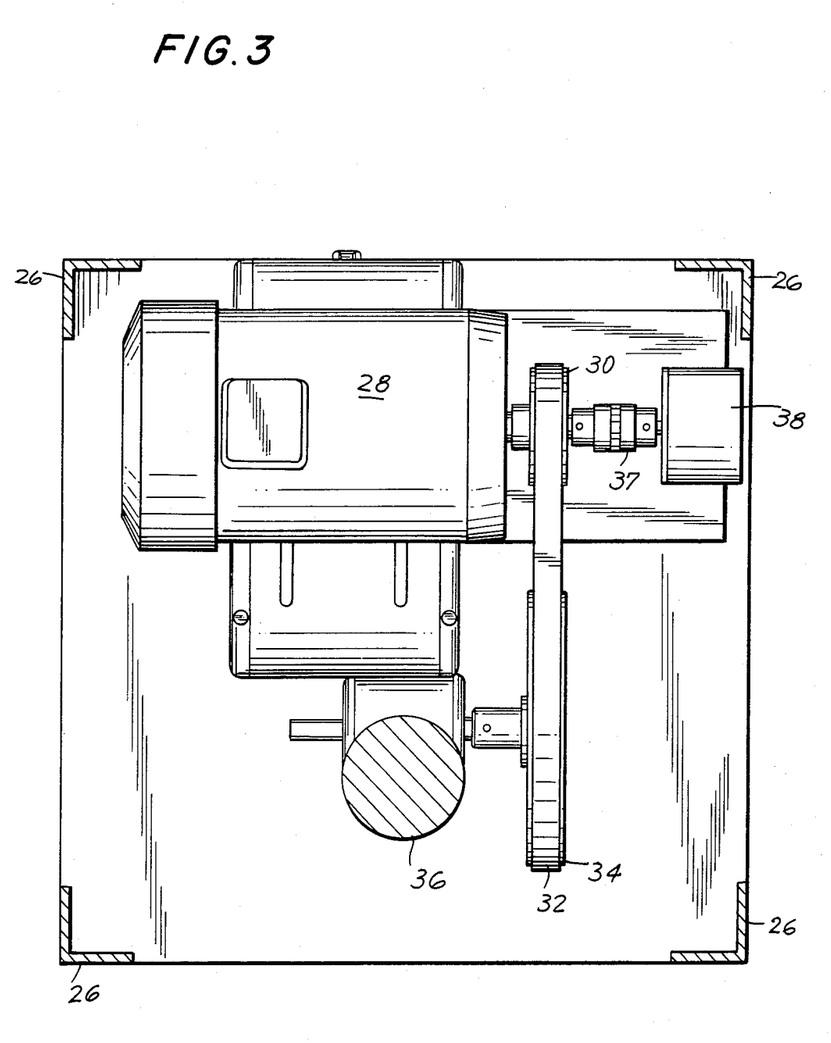
FIG. 3 is a plan view of the bottom section of this embodiment, taken along the line 3—3 in FIG. 2.

With additional reference to FIG. 3, the base assembly 24 includes a DC motor 28 having a timing pulley 30 mounted on its output shaft. A timing belt 32 driven by this pulley 30 in turn drives another timing pulley 34 connected to a ball screw jack 36. A coupling 37 on the output shaft of the motor 28 connects the motor 28 to a digital tachometer 38, which is used to govern the speed of the motor 28.

Figure 4:
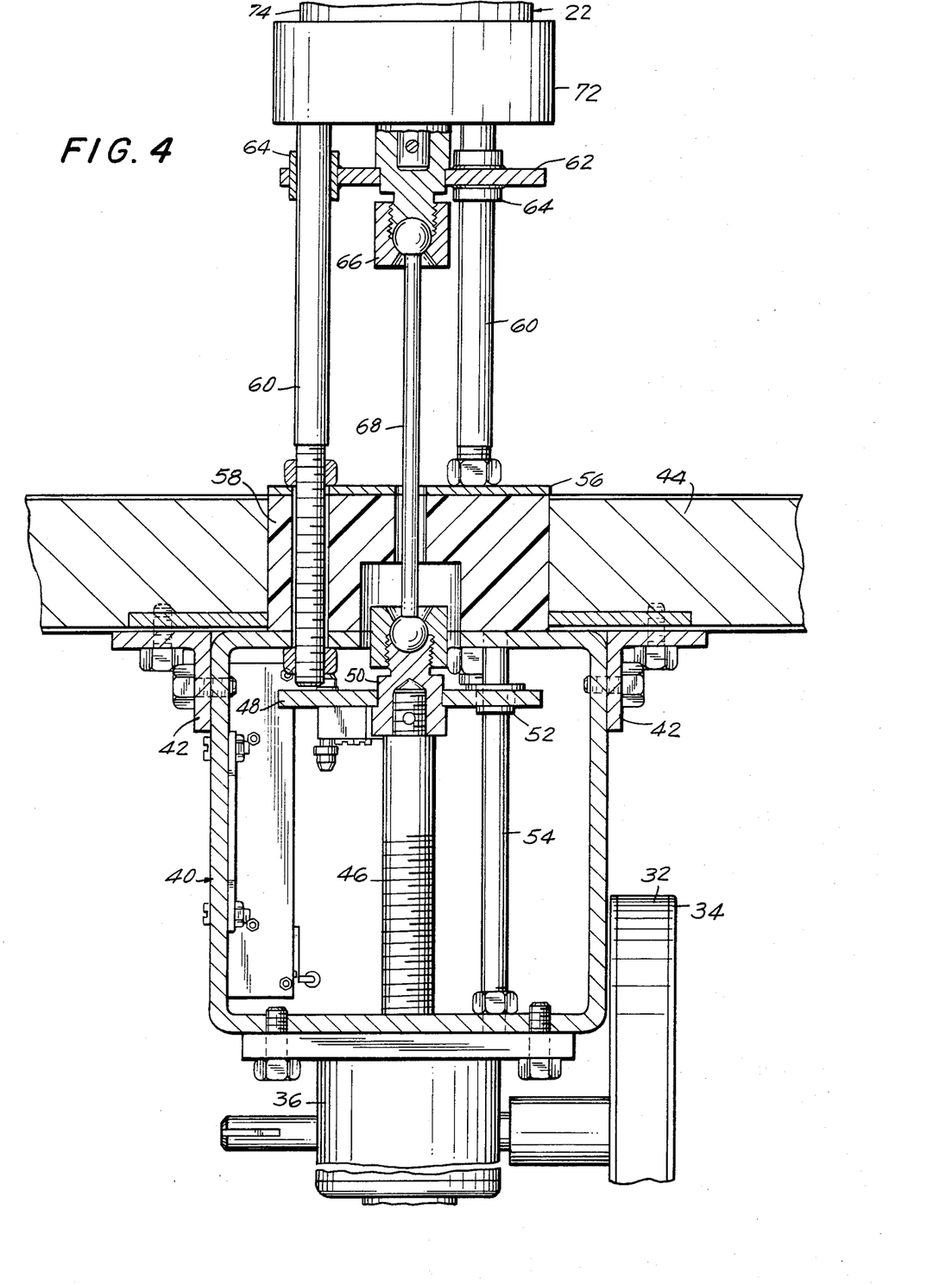
FIG. 4 is a sectional elevation taken along the line 4—4 in FIG. 1.

As illustrated with additional reference to FIG. 4, a frame 40 is mounted by brackets 42 to a lower wall 44 of the oven enclosure 12. This frame 40 also mounts the screw jack 36, and a threaded drive shaft 46 of the latter extends upwards toward the wall 44.

A lower guide plate 48 is mounted on a socket 50 affixed to the top of the shaft 46. This guide plate 48 is provided with cylindrical sleeve bearings 52 which slide upon vertical guide rods 54 also mounted on the frame 40. The guide plate 48 prevents rotation of the shaft 46, but permits axial motion thereof.

A crush plate 56 is mounted on an insulator member 58, and these members are situated in the lower wall 44 of the oven enclosure 12. The crush plate 56 and insulator 58 have central vertical apertures extending therethrough to within the enclosure 12.

A plurality of support shafts 60 rise within the enclosure 12 from the crush plate 56, and an upper guide plate 62 is supported on cylindrical sleeve bearings 64 which slide upon the support shafts 60. A socket 66 is mounted on the upper guide plate 62. A linkage shaft 68 extends vertically through the aperture in the lower crush plate 56 and has lower and upper ball ends seated in the sockets 50 and 66, respectively.

The support shafts 60 are affixed at their upper ends to a lower end cap 72 of the viscosimeter cylinder 22.

Figure 5:
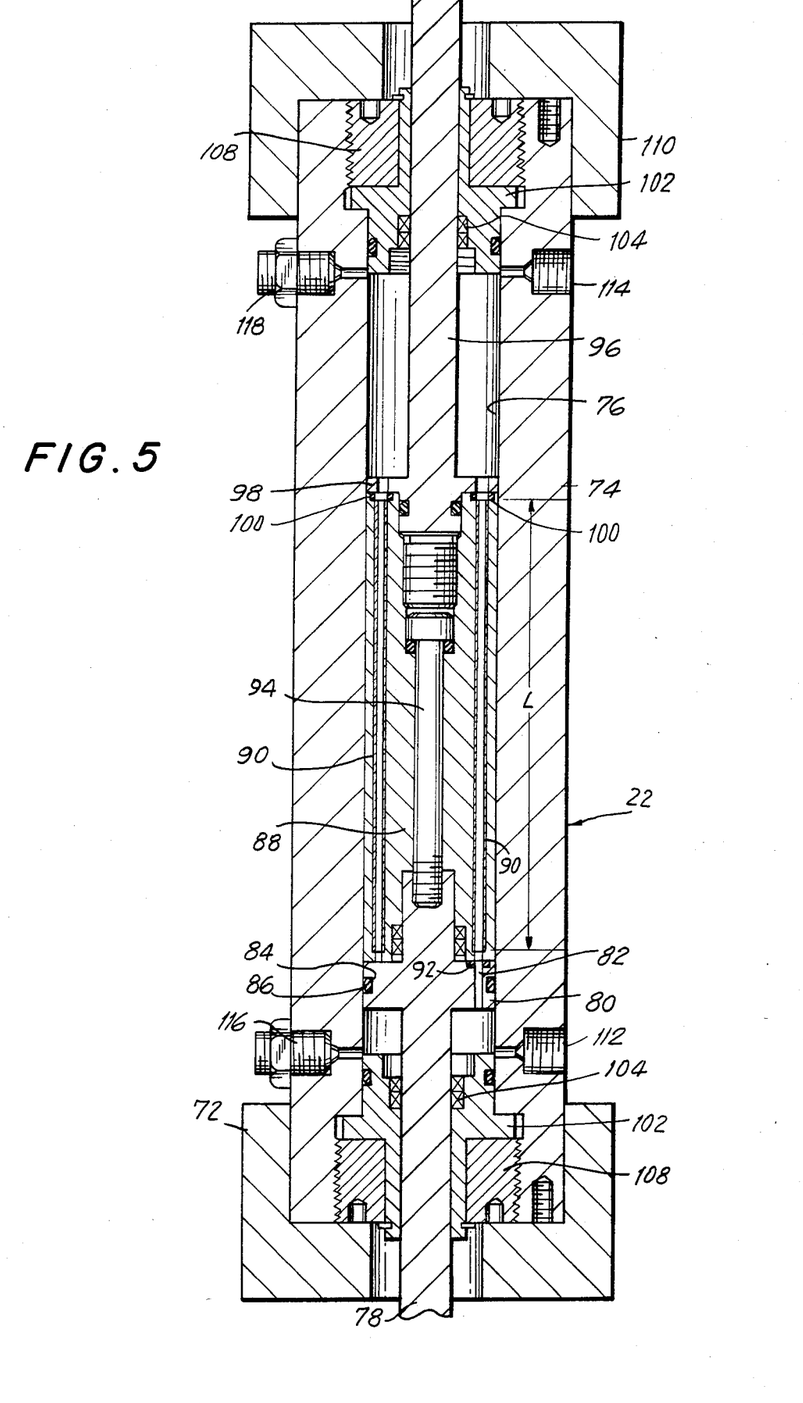
FIG. 5 is a sectional elevation of the viscosimeter cylinder, taken along the lines 5—5 of FIG. 1.

With reference to FIG. 5, the viscosimeter cylinder 22 has a cylindrical barrel 74 with an axial bore 76 formed therein. A drive shaft 78 extends from the socket 66, through the end cap 72, into the bore 76 of the barrel 74. This shaft 78 has, near its end, a selector plate 80 formed unitarily with the shaft 78. The shaft 78 is secured on its outer end to the socket 66 and guide plate 62, which prevents its rotation, but permit axial movement. An axial bore or orifice 82 extends through this selector plate 80. In order to provide sealable sliding contact with the wall of the bore 76, an annular cutout 84 is provided in the circumferential surface 80, and an O-ring seal is seated in this cutout 84, biased against the inner wall of the cylindrical barrel 74.

The piston assembly of this viscosimeter cylinder 22 further includes a main piston body 88 which is rotatable with respect to the selector plate 80. A plurality of capillary tubes 90 are arranged at regular intervals about the axis of the main piston body 88. In this embodiment, there are eight such capillary tubes 90 spaced at forty-five degree intervals. Preferably, these are precision-bore glass capillary tubes, for example, Pyrex tubes manufactured by Corning Glass Works; however, other tubular material may be used with the flow characteristics determined empirically from standard-viscosity fluids. These capillary tubes 90 can each have a different capillary radius R, but should all have the same length L. The length L and radius R for each tube 90 are factory calibrated, and thus are all known precisely.

An O-ring seal 92 is seated in the selector plate 80 about the orifice 82 therein on the face of the selector plate 80 that mates with the selected capillary tube 90. This prevents passage of the test fluid except through the one selected capillary tube 90.

A shoulder bolt 94 rotatably mounts the main piston body 88 onto the shaft 78 against the selector plate 80. A piston plate 98 has a plurality of apertures therein each aligned in registry with a respective one of the capillary tubes 90 in the main piston body 88. This piston plate 98 is affixed to a selector shaft 96. Thus, when the latter is rotated, there is a similar rotation of the main piston body 88, bringing into alignment a capillary tube bore with the axial bore 82 of the selector plate 80 held in a fixed position by the shaft 78 attached to the lower guide mechanism.

O-ring seals are also provided in the main piston body 88 surrounding the ends of the respective capillary tubes 90 at the end facing the piston plate 98.

Seal plugs 102 are seated in each end of the barrel 74 and include poly seals 104 for sealably mounting the shafts 78 and 96. Retaining caps 108 hold these seal plugs 102 in place.

At the end of the cylinder remote from the end cap 72, i.e., at the selector-shaft end of the viscosimeter cylinder 22, there is disposed an upper support cap 110.

Fluid fill ports 112 and 114 are respectively provided at the ends of the cylinder. These ports 112, 114 facilitate the filling and draining of the test fluid into and from the cylinder. Pressure sensors 116 and 118 are disposed in respective ports in the cylinder and are in communication with the fluid on either side of the piston assembly formed of the main piston body 88 and the selector plate 80.

Figures 6, 7:
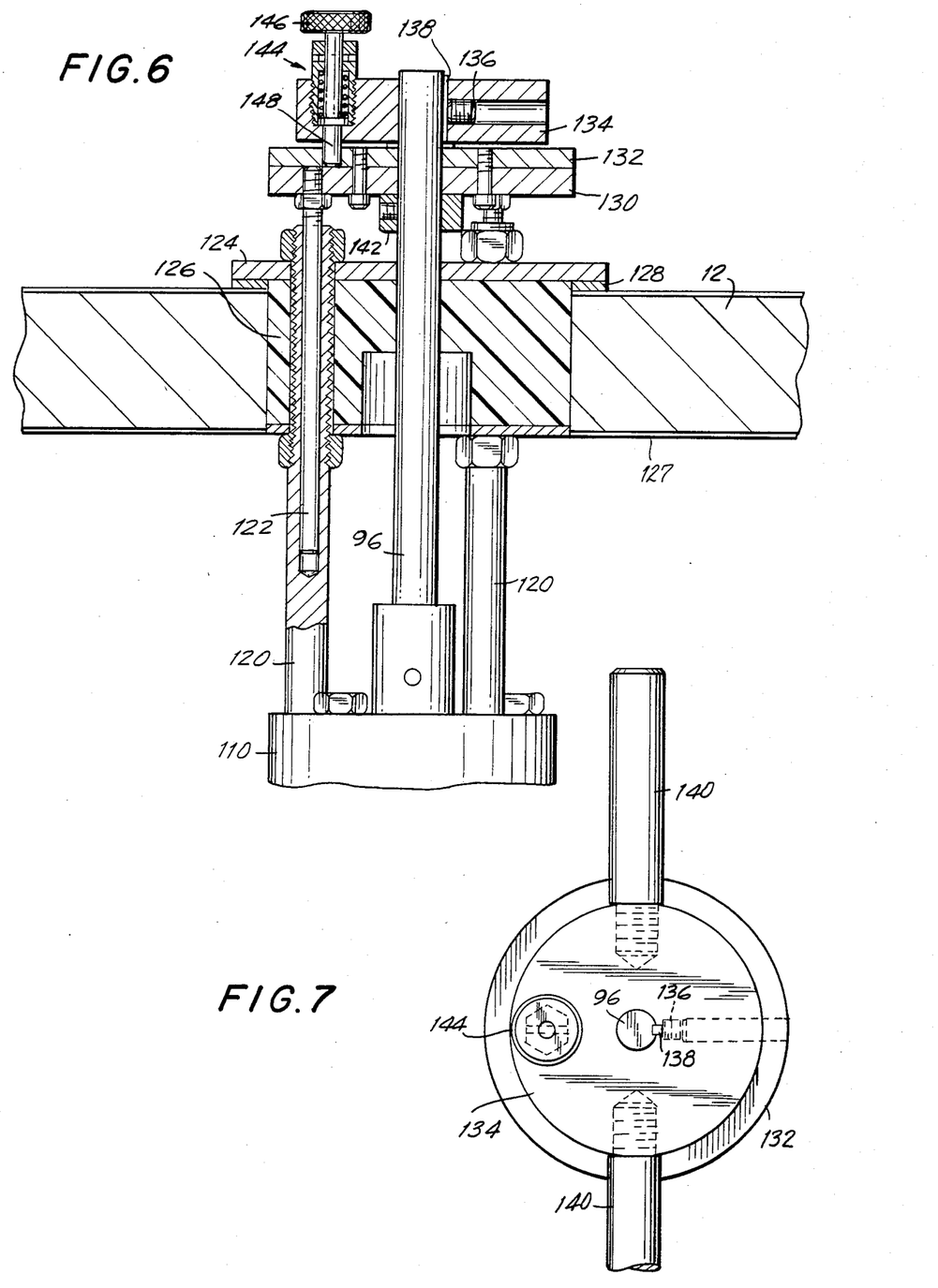
FIG. 6 is a sectional elevation taken along the lines 6—6 of FIG. 1.
FIG. 7 is a partial plan view of the selector handle assembly of this embodiment.

With reference to FIG. 6, the support end cap 110 has a plurality of upper support shafts 120 rising therefrom. These shafts 120 have bores in their upper ends, in which alignment rods 122 are nested.

The support shafts 120 are affixed by threaded nuts to an upper crush plate 124 mounted upon an insulator 126 disposed in an upper wall 127 of the oven enclosure 12. A spacer 128 is here shown between the crush plate 124 and the upper wall 127.

A guide plate 130 is mounted on the upper ends of the alignment rods 122 and is used to transfer the angular alignment of the selector plate 80 and the shaft 78 to the upper orifice selecting mechanism. This guide plate 130 contains a plurality of slotted holes through which pass bolts attached to a selector plate 132, both plates 130 and 132 being rotationally free from the shaft 96. A hub 134 bears a fixed angular relationship to the main piston body 88. Also shown in the drawings are a set screw 136 and key 138. A pair of handles 140 extend from the hub 134 and can be grasped for manually changing the capillary tube 90 that is aligned with the orifice 82 in the selector plate 80.

As shown in FIGS. 6 and 7, the hub 134 is mounted adjacent the selector 132 and a collar 142 is mounted on the shaft below the adjustment plate 130. A lock assembly 144 is fitted into the hub 134, and includes a knob 146 and a spring-loaded shaft 148. A protruding end of the shaft 148 fits into any of eight corresponding slots in the selector plate 132. When it is desired to select a particular capillary tube 90, the knob 146 is pulled up to release the lock assembly 144, and then the handles 140 are turned to rotate the shaft 96 and the associated main piston body 88 relative to the selector plate 80.

Figure 8:
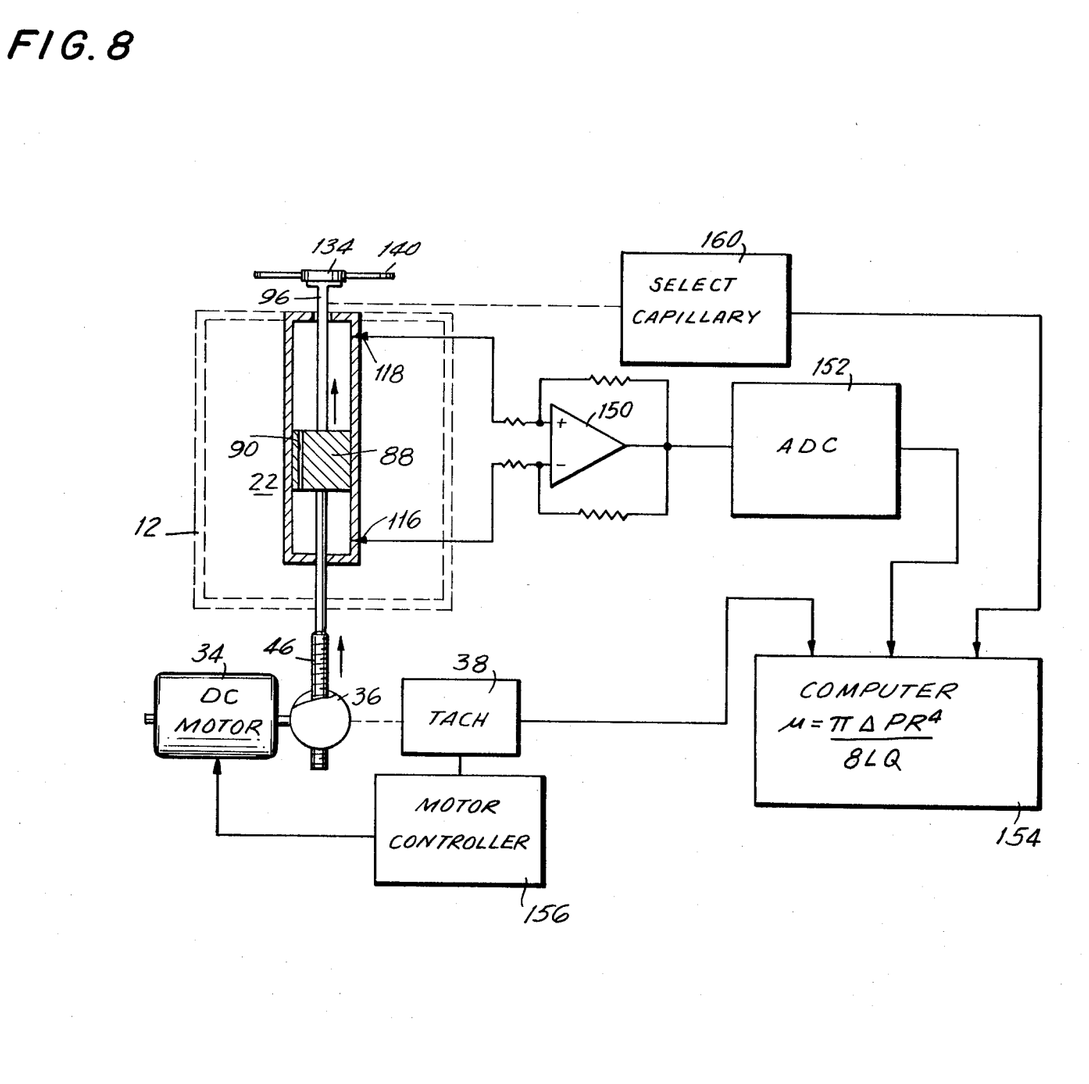
FIG. 8 is a simplified schematic system diagram for explaining the operation of the embodiment of this invention.

The general arrangement of the viscosimeter of this invention, together with associated means for automatically calculating the viscosity of the fluid being tested, will be described with reference to FIG. 8.

As shown in this embodiment, leads from each of the pressure detectors 116 and 118 extend out through the oven enclosure 12 to respective inputs of a differential amplifier 150; the latter provides an output level corresponding to the pressure difference across the selected capillary tube 90 of the viscosimeter main piston body 88. This level is digitized in an analog-to-digital converter 152, and the digitized pressure difference signal therefrom is furnished to a computer 154.

As also shown in this drawing, the tachometer 38 associated with the DC motor 34 supplies a digital speed signal to a digital motor controller 156, and the latter controls the current to the motor 34. Thus, the motor 34, the tachometer 38, and the controller 156 form a servo loop to control the speed at which the piston shaft 78 rises.

The digital signal from the tachometer 38 is also provided to an input of the computer 154, so that the latter knows accurately the speed of movement of the piston 88.

Finally, a capillary selection indicator 160 furnishes to the computer 154 a digital signal corresponding to the one of the various capillary tubes 90 of the main piston body 88 that has been selected by rotation of the selector handles 140. This information can be entered manually, or, as indicated by the dashed line in this drawing, means associated with the shaft 96 can interact with the capillary selection indicator 160 to provide the proper data automatically upon rotation of the shaft 96.

The drive system described herein is formed of a DC motor with a tachometer speed indicator in a closed control feedback loop. Other forms of drive systems using synchronous or stepper motors, responding to frequency control, in both open and closed loop control circuits, can be used for the viscosimeter displacement function.

The data corresponding to the capillary tube length L and the effective radius R for each capillary tube 90 are stored in the computer 154. Further, data corresponding to the effective area of the bore 76 of the viscosimeter barrel 74 are stored in the computer 154. Consequently, based on the data from the tachometer 38, the computer can automatically calculate the appropriate value Q corresponding to the volume rate of transfer of the fluid being tested through the selected capillary tube 90.

The digitized data from the converter 152 correspond to the pressure head ΔP as sensed by the pressure detectors 116 and 118. From these data, the viscosity $\mu$ is automatically calculated by the computer, employing Poiseuille's equation, $$\mu = \frac{\pi \Delta P R^4}{8 L Q}$$

Terms and expressions employed in this description are terms of description and not of limitation, there being no intention in the use of such terms and expressions of excluding any equivalents of the features shown and described or portions thereof. Further, terms of orientation are intended for use only in explaining the described embodiment, the invention of course being capable of practice in any desired orientation.

While a particular embodiment of this invention has been described in detail hereinabove with reference to the drawings, it should be understood that the principles of this invention can be employed in many modifications and variations of this embodiment without departure from the scope and spirit of the present invention, as defined in the appended claims:

What is claimed is:

1. Differential pressure viscosimeter for measuring the viscosity of a fluid, comprising
   a hollow pressure cylinder having first and second ends and an interior wall, the cylinder including means for receiving a fill of said fluid for measuring its viscosity;
   a piston disposed for axial movement in said cylinder and sealably contacting the interior wall thereof, the piston including a capillary passage extending axially through said piston to permit passage of said fluid therethrough;
   means for driving said piston at a controlled speed axially within said cylinder so that said fluid is displaced from the first end to the second end thereof through said capillary passage; and
   pressure monitoring means disposed in fluid communication with the interior of said cylinder for measuring the pressure differential in said fluid across said capillary passage while said piston is being driven.

2. Differential pressure viscosimeter for measuring the viscosity of a fluid, comprising
   a hollow pressure cylinder having first and second ends and an interior wall, the cylinder including means for receiving a fill of said fluid for measuring its viscosity;
   a piston disposed for axial movement in said cylinder and sealably contacting the interior wall thereof, including a capillary passage extending axially through said piston to permit passage of said fluid through said passage;
   a drive shaft connected to said piston and extending through the first end of said cylinder;
   a drive assembly coupled to said drive shaft and fixedly mounted relative to said cylinder for driving said piston axially in said cylinder, said drive assembly including a frame, bracket means mounting said cylinder relative to said frame, a controllable electric motor having an axle, a tachometer mounted on said axle and providing signal indicative of the speed of the motor axle, a jack driven by said motor axle translating rotational motion of said axle into linear motion for driving said drive shaft, and control means for controlling the current to said motor in response to said signal; and
   pressure monitoring means disposed in fluid communication with the interior of said cylinder for measuring the pressure differential in said fluid across said capillary passage while said piston is being driven.

3. Differential pressure viscosimeter for measuring the viscosity of a fluid, comprising
   a hollow pressure cylinder having first and second ends and an interior wall, the cylinder including means for receiving a fill of said fluid for measuring its viscosity;
   a piston disposed for axial movement in said cylinder and sealably contacting the interior wall thereof, the piston including a capillary passage extending axially through said piston to permit passage of said fluid through said passage;
   drive means coupled to said piston for driving said piston axially relative to said cylinder, so that the fluid in said cylinder is displaced through said passage;
   oven enclosure means for enclosing the cylinder, the latter being mounted therewithin, to maintain said cylinder at a temperature representative of the natural conditions of said fluid; and
   pressure monitoring means disposed in fluid communication with the interior of said cylinder for measuring the pressure differential in said fluid across said capillary passage while said piston is being driven.

4. Differential pressure viscosimeter for measuring the viscosity of a fluid, comprising
   a hollow pressure cylinder having first and second ends and an interior wall, the cylinder including means for receiving a fill of said fluid for measuring its viscosity;
   a piston disposed for axial movement in said cylinder and sealably contacting the interior wall thereof, the piston including main piston body having a plurality of capillary passages disposed circumferentially about the axis of said piston and each extending axially through said main piston body, said piston further including a selector plate having an aperture therethrough and alignable with a selected one of said capillary passages to permit flow of said fluid through and only through the selected passage;
   means for driving said piston at a controlled speed axially within said cylinder so that said fluid is displaced through said selected capillary passage;
   selecting means extending external to said cylinder for selectively rotating said selector plate relative to said main piston body to select a desired one of said capillary passages; and pressure monitoring means disposed in fluid communication with the interior of said cylinder for measuring the pressure differential in said fluid across the selected capillary passage while said piston is being driven.

5. Differential pressure viscosimeter according to claim 4, wherein said piston selector plate has an annular groove in an outer cylindrical surface thereof, and a sealing ring disposed in said annular groove and biased against the interior wall of said cylinder.

6. Differential pressure viscosimeter according to claim 4, wherein said piston selector plate has a face disposed against an end of said main piston body with said aperture opening into said face, and a sealing ring disposed in said face and biased against said end of the main piston body to seal said aperture with the selected capillary passage aligned therewith.

7. Differential pressure viscosimeter for measuring the viscosity of a fluid, comprising
- a hollow pressure cylinder having first and second ends and an interior wall, the cylinder including means for receiving a fill of said fluid for measuring its viscosity;
- a piston disposed for axial movement in said cylinder and sealably contacting the interior wall thereof, the piston including a main piston body having a plurality of capillary passages disposed circumferentially about the axis of said piston and each extending axially through said main piston body, said piston further including a selector plate having an aperture therethrough alignable with a selected one of said capillary passages to permit flow of said fluid through and only through the selected passage;
- a drive shaft connected to one of said main piston body and said selector plate and extending through the first end of said cylinder;
- a drive assembly coupled to said drive shaft and fixedly mounted relative to said cylinder for driving said piston axially in said cylinder;
- a selector shaft affixed to the other of said main piston body and said selector plate and extending out from the second end of said cylinder;
- selector means on said selector shaft for rotating the same to effect mutual rotation of said main piston body with said selector plate for selectively aligning said aperture with a desired one of said capillary passages; and
- pressure monitoring means disposed in communication with the fluid at the first and second ends of said cylinder for measuring the pressure differential in said fluid across the selected capillary passage while said piston is being driven.

8. Differential pressure viscosimeter for measuring the viscosity of a fluid, comprising
- a hollow pressure cylinder having first and second ends and an interior wall, the cylinder including means for receiving a fill of said fluid for measuring its viscosity;
- a piston disposed for axial movement in said cylinder and sealably contacting the interior wall thereof, the piston including a main piston body having eight capillary tubes, each having a passage of a different radius, spaced circumferentially 45° apart about the axis of said piston and each extending axially through said main piston body, said piston further including a selector plate having an aperture therethrough alignable with a selected one of said capillary passages to permit passage of said fluid through and only through the selected passage;
- a drive shaft connected to one of said main piston body and said selector plate and extending through the first end of said cylinder;
- a drive assembly coupled to said drive shaft and fixedly mounted relative to said cylinder for driving said piston axially in said cylinder;
- a selector shaft affixed to the other of said main piston body and said selector plate and extending out from the second end of said cylinder;
- a selector device coupled to said selector shaft for rotating the same to effect mutual rotation of said main piston body with said selector plate for selectively aligning said aperture with a desired one of said capillary passages; and
- pressure monitoring means disposed in communication with the first and second ends of said cylinder for measuring the pressure differential in said fluid across the selected capillary passage while said piston is being driven.

9. Differential pressure viscosimeter according to claim 8, wherein said capillary tubes are glass tubes each disposed in a respective axial bore within said main piston body.

10. Differential pressure viscosimeter for measuring the viscosity of a fluid, comprising
- a hollow pressure cylinder having first and second ends and an interior wall, the cylinder including means for receiving a fill of said fluid for measuring its viscosity;
- a piston disposed for axial movement in said cylinder and sealably contacting the interior wall thereof, the piston including a main piston body having a plurality of capillary passages disposed circumferentially about the axis of said piston and each extending axially through said main piston body, said piston further including a selector plate having an aperture therethrough selectively alignable with said capillary passages to permit passage of said fluid through and only through the selected passage;
- a drive shaft connected to one of said main piston body and said selector plate and extending through the first end of said cylinder;
- a drive assembly coupled to said drive shaft and fixedly mounted relative to said cylinder for driving said piston axially in said cylinder, said drive assembly including a frame, bracket means mounting said cylinder relative to said frame, a controllable electric motor having an axle, a tachometer mounted on said axle and providing a signal indicative of the speed of the motor axle, a jack driven by said motor axle for driving said drive shaft axially, and control means for controlling the current to said motor in response to said signal;
- a selector shaft affixed to the other of said main piston body and said selector plate and extending out from the second end of said cylinder;
- a selector handle on said selector shaft for rotating the same to effect mutual rotation of said main piston body with said selector plate for selectively aligning said aperture with a desired one of said capillary passages; and pressure monitoring means disposed in fluid communication with the interior of said cylinder for measuring the pressure differential in said fluid across the selected capillary passage while said piston is being driven.

11. Differential pressure viscosimeter for measuring the viscosity of a fluid, comprising a hollow pressure cylinder having first and second ends and an interior wall, the cylinder including means for receiving a fill of said fluid for measuring its viscosity;

a piston disposed for axial movement in said cylinder and sealably contacting the interior wall thereof, the piston including a main piston body having a plurality of capillary passages disposed circumferentially about the axis of said piston and each extending axially through said main piston body said piston further including a selector plate having an aperture therethrough alignable with a selected one of said capillary passages to permit passage of said fluid through and only through the selected passage;

a drive shaft connected to one of said main piston body and said selector plate and extending through the first end of said cylinder;

a drive assembly coupled to said drive shaft and fixedly mounted relative to said cylinder for driving said piston axially in said cylinder;

a selector shaft affixed to the other of said main piston body and said selector plate and extending out from the second end of said cylinder;

an oven enclosure having side walls, a first end wall, and a second end wall, the oven enclosure enclosing the cylinder, with the latter being fixedly mounted therewithin, to maintain said cylinder at a temperature representative of the natural conditions of said fluid; said drive assembly being mounted at said first end wall with said drive shaft passing therethrough, said selector shaft passing through said second end wall;

a selector device on said selector shaft situated outside said oven enclosure for rotating the same to effect mutual rotation of said main piston body and said selector plate for selectively aligning said aperture with a desired one of said capillary passages; and pressure monitoring means disposed at said first and second ends of said cylinder for measuring the pressure differential in said fluid across the selected capillary passage while said piston is being driven.

12. Differential pressure viscosimeter according to claim 11, wherein said drive assembly includes a frame and a jack mounted on said frame and having a linearly movable output shaft; and said oven enclosure includes a first crush plate in said first end wall, said frame being mounted onto said first crush plate; said viscosimeter further comprising a plurality of support members within said oven enclosure each affixed to said first crush plate and to said first end of said cylinder; a shaft support member slidably mounted on said support members for axial movement relative to said cylinder, said drive shaft being mounted on said shaft support member; and a linkage connecting said with said shaft support member to effect the axial driving of said piston.

13. Differential pressure viscosimeter according to claim 11, wherein said oven enclosure includes a crush plate in said second end wall, the crush plate having a passage therein for said selector shaft; a plurality of support rods mounted relative to said crush plate and extending into said oven enclosure to support the second end of said cylinder; a plurality of alignment rods adjustably supported on said guide rods; and said selector device includes a selector plate mounted on said alignment rods externally of said oven enclosure, a selector hub fixed on said selector shaft adjacent said selector plate, and orifice selector means coupled to said hub to rotate the same relative to said selector plate.

14. Differential pressure viscosimeter according to claim 13, wherein said selector device further includes a selection lock mounted on said hub to lock the same to said selector plate against mutual rotation, said lock being selectively releasable for selection of a desired one of said capillary passages.

* * * * *